United States Patent
Mittermeier et al.

[11] Patent Number: 6,063,037
[45] Date of Patent: May 16, 2000

[54] BONE MARROW BIOPSY NEEDLE

[75] Inventors: Manfred Mittermeier, Northfield; Alan M. Hable, Wheeling, both of Ill.

[73] Assignee: Manan Medical Products, Inc., Northbrook, Ill.

[21] Appl. No.: 09/137,854

[22] Filed: Aug. 21, 1998

[51] Int. Cl.$^7$ .................................................. A61B 10/00
[52] U.S. Cl. ............................................................ 600/567
[58] Field of Search .......................... 600/567; 128/753, 128/754

[56] References Cited

U.S. PATENT DOCUMENTS

| | | | |
|---|---|---|---|
| 3,844,291 | 10/1974 | Moen | 128/354 |
| 4,403,617 | 9/1983 | Tretinyak | 128/754 |
| 4,630,616 | 12/1986 | Tretinyak | 128/753 |
| 4,651,752 | 3/1987 | Fuerst | 128/754 |
| 4,655,226 | 4/1987 | Lee | 128/754 |
| 4,785,826 | 11/1988 | Ward | 128/754 |
| 4,838,282 | 6/1989 | Strasser et al. | 128/754 |
| 5,074,311 | 12/1991 | Hasson | 128/754 |
| 5,148,813 | 9/1992 | Bucalo | 128/754 |
| 5,172,700 | 12/1992 | Bencini et al. | 128/751 |
| 5,286,255 | 2/1994 | Weber | 604/22 |
| 5,318,589 | 6/1994 | Lichtman | 606/205 |
| 5,333,619 | 8/1994 | Burgio | 128/754 |
| 5,357,974 | 10/1994 | Baldridge | 128/754 |
| 5,462,062 | 10/1995 | Rubenstein et al. | 128/754 |
| 5,595,186 | 1/1997 | Rubenstein et al. | 128/754 |
| 5,634,473 | 6/1997 | Goldenberg et al. | 128/754 |

*Primary Examiner*—Max Hindenburg
*Assistant Examiner*—Brian Szmal
*Attorney, Agent, or Firm*—Dick & Harris

[57] ABSTRACT

The present invention is directed to a biopsy needle for extracting bone marrow from a living bone. The biopsy needle comprises an outer cannula, an inner cannula slidable therein, an obturator and an ejector rod. The outer cannula has a proximal end, affixed to a handle, and a distal end which has a tapered inner diameter. The inner cannula likewise has a proximal end, affixed to an interlocking handle, and a distal end. The inner cannula distal ends consists of a tissue receiving region and a tissue grasping mechanism. The tissue grasping mechanism comprises a resilient deformable wall with an asymmetric configuration, preferably, two opposing slits, and a structure-maintaining spanning member. The tissue grasping member is which are deformed and at least partially closed upon insertion into the tapered region of the outer cannula. In operation, this deformation severs a tissue sample into the receiving region of the inner cannula, which may then be withdrawn from a patient. A spring biased ejector rod displaces the sample from the inner cannula, while also reforming the tissue grasping portion of the inner cannula to its original pre-biopsy shape. The obturator may be used in combination with the outer cannula for initial insertion of the needle into the patient.

19 Claims, 3 Drawing Sheets

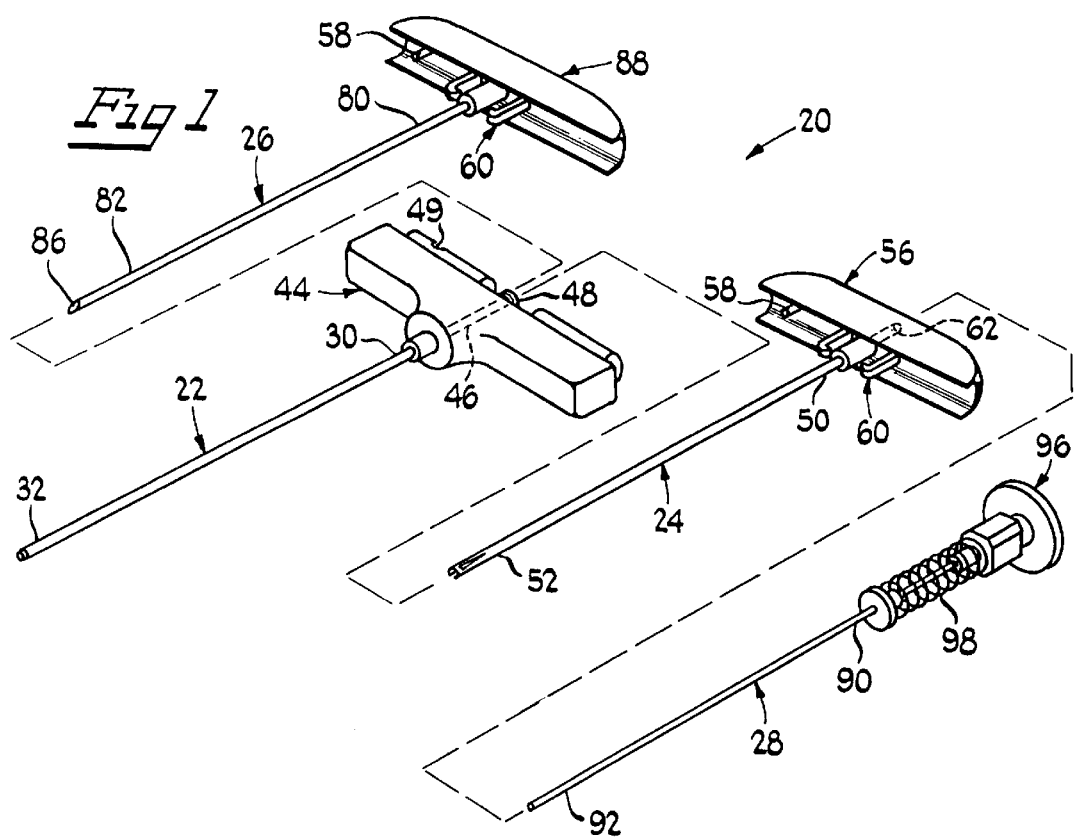
Fig 1
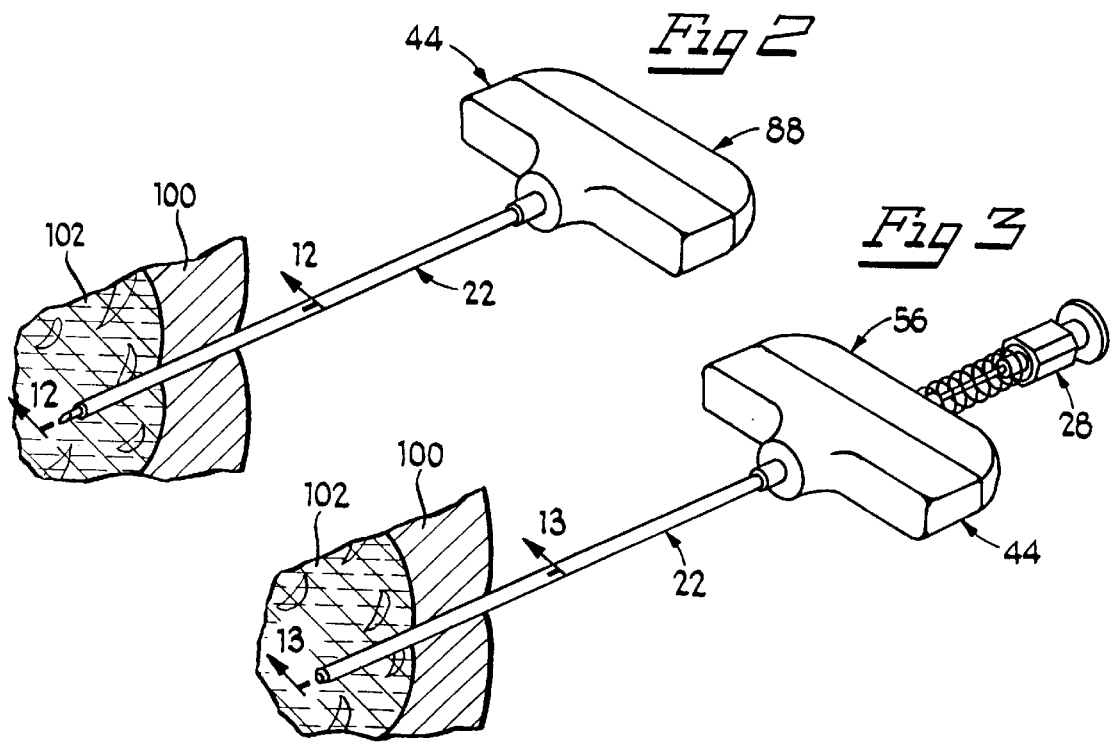
Fig 2
Fig 3

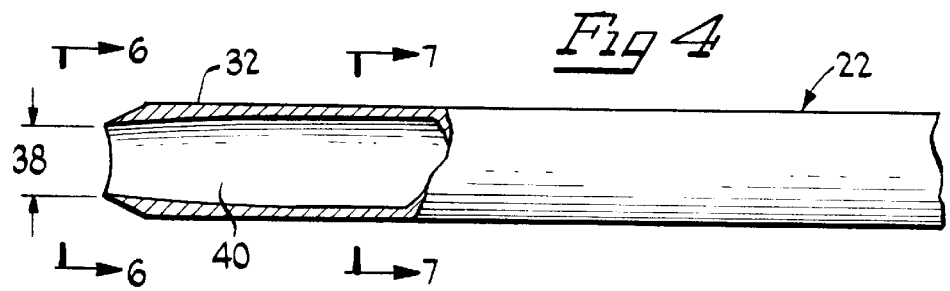
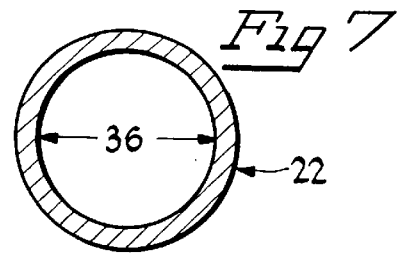
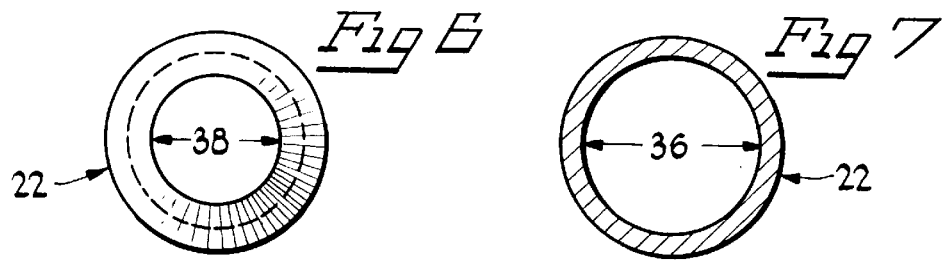
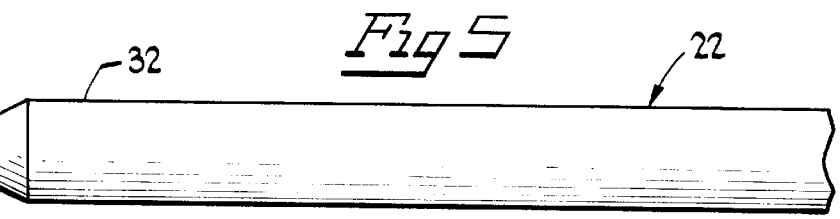
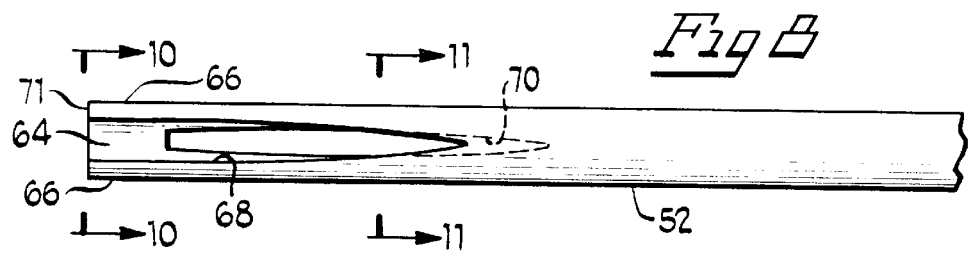
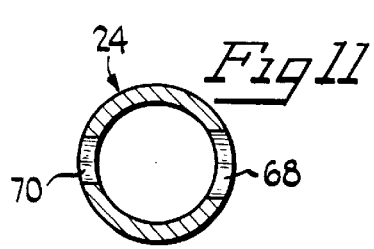
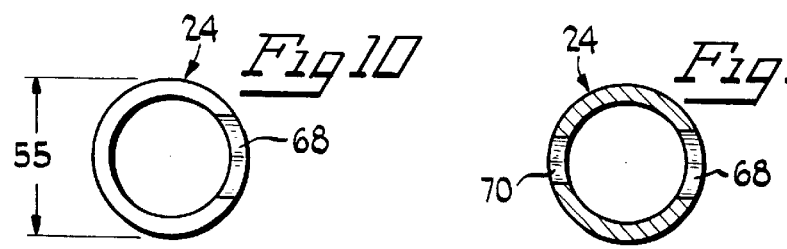
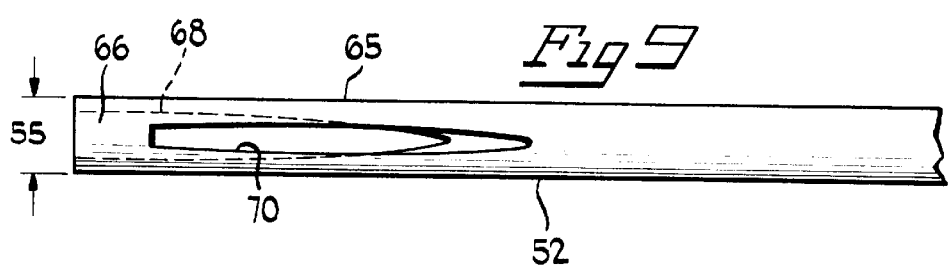

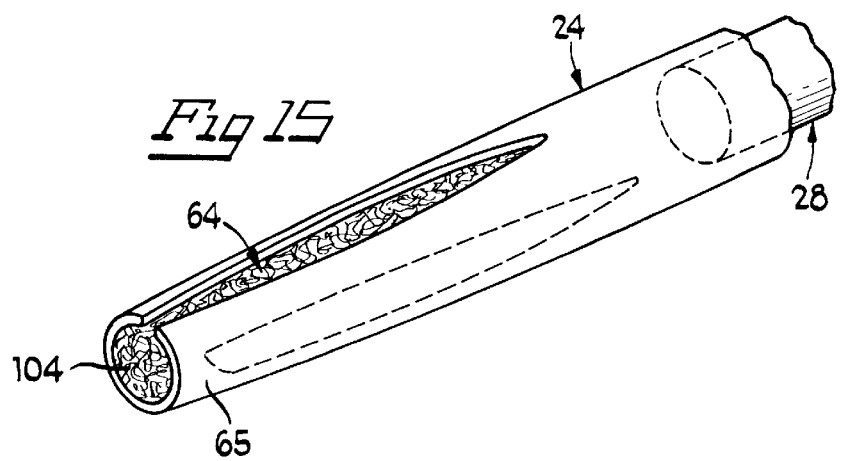
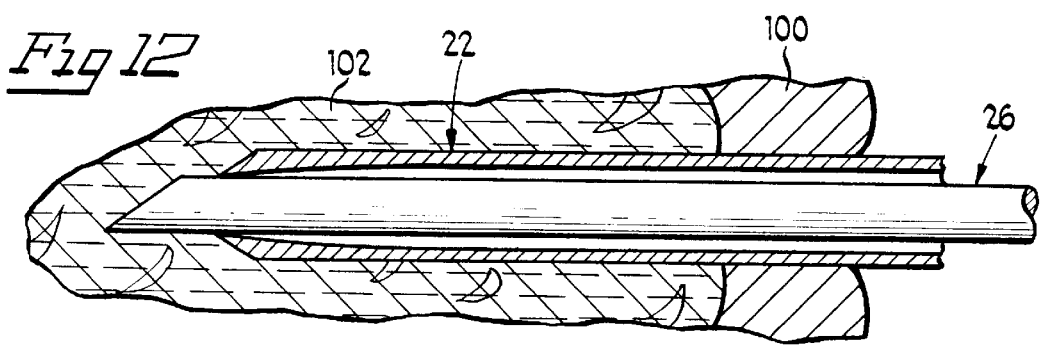
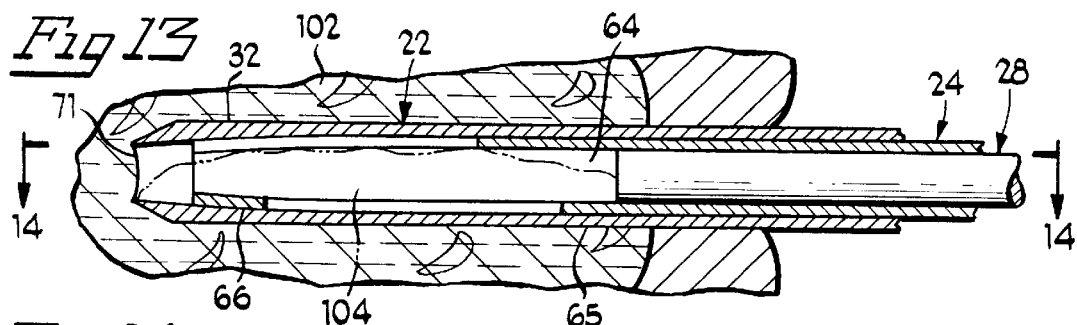
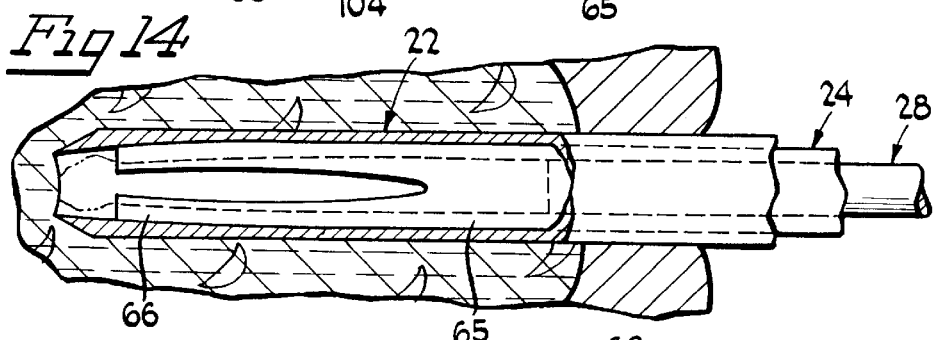
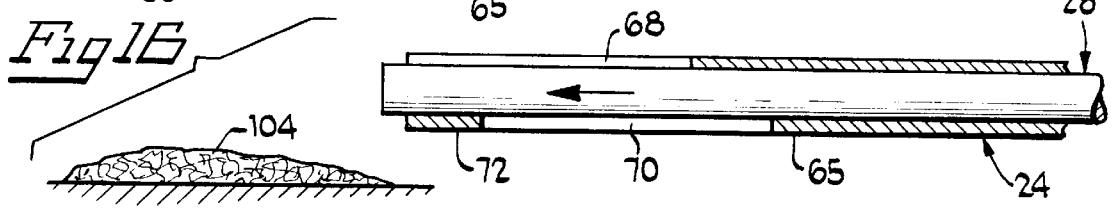

BONE MARROW BIOPSY NEEDLE

BACKGROUND OF THE INVENTION

1. Field of the Invention

The present invention relates in general to medical devices and, in particular, to a biopsy needle for harvesting bone marrow samples from a living bone.

2. Background Art

Bone marrow biopsy needles have been known in the art for many years. In particular, many of these needles consist of a hollow outer cylinder with a hollow inner cylinder slidable therewithin. The outer cylinder conventionally consists of a proximal end with some form of a handle and a distal end with a tapered diameter. The distal end is typically sharp, so as to allow the needle to bore through both soft and hard tissue. The hollow inner cylinder, on the other hand, typically has a distal end consisting of some form of a cutting member. The cutting member serves to sever a tissue sample from a soft tissue mass and secure the sample inside the hollow inner cylinder, before withdrawing the sample from the patient.

For instance, Burgio, U.S. Pat. No. 5,333,619, discloses a method for rigid tissue biopsy using a partial cannula within a standard hollow outer needle having a tapered end. The partial cannula is introduced into the needle when the needle has already been inserted into the tissue. To obtain the biopsy sample, the needle is rotated repeatedly in the same direction about its major axis, thus breaking off the biopsy sample into the hollow tapered portion of the needle.

In contrast, Rubinstein, U.S. Pat. No. 5,462,062, discloses a bone marrow biopsy needle with hinged blades that cut and retain a biopsy sample. The biopsy needle consists of an outer cannula with an inwardly tapered distal end, and an inner cannula having a pair of opposing blades hingedly connected to its distal end. Specifically, upon prolapsing of tissue into the outer cannula, the inner cannula is advanced forcing its hinged ends into contact with the tapered end of the outer cannula. At this point, the hinged ends are directed radially inward, thereby cutting off the biopsy core and retaining it inside the needle.

Like Rubinstein '062, U.S. Pat. No. 4,785,826 by Ward discloses a biopsy needle with a tapered outer cannula and an inner cannula positionable therein. However, instead of hinged blades, the distal end of the inner cannula in Ward '826 comprises a series of flexible, sharp, tissue capturing segments arranged in a starburst pattern. Those segments deform and close upon engagement with the tapered end of the outer cannula, thus severing the tissue housed within the device. Moreover, while the inner cannula in Rubinstein '062 is freely slidable, Ward '826 teaches the coupling of the outer cannula to the inner cannula by the mating of male and female threaded members.

Finally, Rubinstein, U.S. Pat. No. 5,595,186, discloses a bone marrow biopsy needle that utilizes a forceps-type member to obtain a sample beyond the distal end of the outer cannula. In particular, the outer cannula narrows at its distal end, thus urging pincers, positioned at the distal end of an inner tube, together until they close upon themselves beyond the opening of the distal end of the outer cannula. Upon closing, the pincers sever a tissue sample for removal from the bone.

Although these bone biopsy devices have worked well, they have experienced certain limitations. For example, many of these devices require needle movement while inside a patient's bone to sever the soft tissue sample. This movement may take the form of rotation of the inner cannula relative to the outer cannula, or vice versa, or a certain amount of horizontal or vertical movement of the needle itself inside the bone. Inasmuch as any additional movement of the needle results in potential patient discomfort and a larger wound or needle bore hole, it is a goal in the art to minimize any needle movement.

Moreover, other biopsy needles making use of inner canulas having pincers or other flexible tissue grasping portions have experienced other difficulties. In particular, the flexibility required in the tissue grasping portion of the inner cannula to clamp and sever a tissue sample from the tissue mass upon contact with the tapered end of the outer cannula leads to problems with inner cannula durability. Specifically, the tissue grasping portion of the inner canula must possess the flexibility to conform to the outer cannula taper, the strength to sever the tissue sample, and the durability and memory to readily return to its original form for repeated use. Current devices employ tissue grasping regions that are flexible enough to deform, but lack the structural integrity to return readily and easily to their original shape for repeated use. Thus, it is a goal in the art to create a tissue grasping mechanism that has both the flexibility and durability required for effective and repetitive tissue sampling on the same patient, during the same procedure. All elements of such a device are disposable after the procedure.

SUMMARY OF THE INVENTION

The present disclosure is directed to a bone marrow biopsy needle for insertion into and through a mass of bone to retrieve a biopsy sample of bone marrow tissue. The bone marrow biopsy needle comprises an outer cannula, an inner cannula, an obturator, and an ejector rod. The outer cannula consists of substantially hollow cylindrical tube having both proximal and distal ends. Although the outer cannula has a pre-determined inner diameter to accept the inner cannula, the distal end inner diameter is tapered, thus defining a tissue engaging region. Moreover, the outer cannula distal end preferably has a saddle point configuration with sharp edges, to facilitate tissue and bone penetration.

In a preferred embodiment, the proximal end of the outer cannula is affixed to a T-shaped handle, having a bore hole with an inner diameter substantially equivalent to the inner diameter of the outer cannula. The T-shaped handle preferably consists of locking means designed to work in combination with the inner cannula and obturator handles. Such a locking means prevents the biopsy needle components from moving when positioned inside a patient, thus providing a physician with greater control over the biopsy procedure.

The inner cannula likewise consists of a substantially hollow cylindrical tube having both proximal and distal ends. The inner cannula has an outer diameter which is narrower than the inner diameter of the outer cannula proximal end, but wider than the inner diameter of the tapered outer cannula distal end. Such an outer diameter allows the inner cannula to slide freely inside the outer cannula until it reaches and is deformed by the tapered portion of the distal end.

In a preferred embodiment, the proximal end of the inner cannula is also affixed to a T-shaped handle. The T-shaped handle is configured to enter into a locking orientation with the outer cannula T-shaped handle. Moreover, the inner cannula T-shaped handle consists of hole, through which the ejector rod may be inserted.

At its distal end, the inner cannula consists of a tissue receiving region having at least two or more interruptions in the continuity of the inner cannula. At least two of the interruptions are different from one another in at least one of configuration and orientation to alter the malleable memory of the tissue receiving portion of the inner cannula. These interruptions further define a tissue grasping member. The tissue grasping member preferably comprises a resilient deformable wall, a first slit, a second slit, and distal edge, and a spanning member. While the first slit is positioned in a first side of the resilient deformable wall, the second slit preferably is displaced approximately 180 degrees from the first slit in a second side of the resilient deformable wall. Moreover, while the first slit extends from the distal edge toward the proximal end of the inner cannula, the second slit extends from a point slightly displaced from the distal edge of the inner cannula toward the proximal end, thus defining the spanning member.

In a preferred embodiment, the spanning member connects both sides of the second slit, thus providing the tissue grasping member with increased structural integrity. In particular, while the first and second slits provide the tissue grasping portion of the inner cannula with flexibility and deformability, the spanning member imparts the structural strength, integrity, and malleability required for the tissue grasping member to retain biopsy tissue samples, release those samples, and return to its original pre-deformation shape.

Also in a preferred embodiment, the obturator is a substantially solid cylindrical rod having proximal and distal ends. The obturator has an outer diameter pre-determined to be freely slidable within the outer cannula. At its proximal end, the obturator has a T-shaped handle substantially similar to that on the inner cannula. At its distal end, the obturator has a cutting point. In a preferred embodiment, the distal end of the obturator extends beyond and seals the distal end of the outer cannula, thus preventing any tissue from entering the outer cannula during insertion into a patient.

Likewise, the ejector rod comprises a substantially solid cylindrical rod having both proximal and distal ends. However, the ejector rod preferably has an outer diameter pre-determined to be freely slidable within the inner cannula. The proximal end is affixed to an ejector knob, which is associated with a spring. While the ejector rod is of a sufficient length to eject all of a biopsy sample from the inner cannula upon spring compression, the spring biasing ensures that the rod does not interfere with the biopsy procedure.

In operation, the obturator and outer cannula, in a locked orientation, are inserted into the biopsy tissue sampling region of a patient. Once the outer cannula reaches the tissue sampling region, the obturator is withdrawn and the outer cannula is advanced forward into bone marrow, thus forcing tissue to enter the distal engaging region of the outer cannula. At this point, inner cannula and ejector rod are inserted into the proximal end of the outer cannula and directed toward the tapered engaging region. Upon reaching the tapered region, the resilient deformable wall of the inner cannula tissue grasping member is deformed inwardly under force of the outer cannula inner walls to a tissue sampling orientation, thus isolating and severing a tissue sample into the tissue receiving region of the inner cannula. Indeed, inasmuch as the inner cannula locks into the outer cannula upon complete advance therein, neither additional rotation nor additional horizontal or vertical movement of either cannula is required to sever the tissue sample.

The inner cannula is then withdrawn, either alone or in combination with the outer cannula, from the patient with the tissue sample housed in the tissue receiving region. The tissue sample is subsequently dislodged upon pressing the ejector knob, which overcomes the spring bias of the ejector rod. While ejecting the tissue sample, the ejector rod performs the additional function of reforming the resilient deformable wall of the tissue grasping member of the inner cannula to a tissue releasing orientation and its original pre-biopsy configuration. To this end, the ejector rod re-expands the cinched portions of the spanning member and the resilient deformable wall which were at least partially closed upon contact with the tapered region of the outer cannula. Indeed, the structural integrity provided to the tissue grasping member by the spanning member allows complete reformation and recovery.

BRIEF DESCRIPTION OF THE DRAWINGS

FIG. 1 of the drawings is an exploded perspective view of all four components of the bone marrow biopsy needle system, according to the present invention;

FIG. 2 of the drawings is a perspective view of the biopsy needle, with obturator, being inserted into a tissue sampling region according to the present invention;

FIG. 3 of the drawings is a perspective view of the biopsy needle, with inner cannula and ejector rod, in a tissue sampling orientation according to the present invention;

FIG. 4 of the drawings is a side elevational view, partially cross-sectioned, of the outer cannula according to the present invention;

FIG. 5 of the drawings is a side elevational view of the outer cannula according to the present invention;

FIG. 6 of the drawings is a cross-sectional view of FIG. 4 taken along the lines 6—6 and looking in the direction of the arrows;

FIG. 7 of the drawings is a cross-sectional view of FIG. 4 taken along the lines 7—7 and looking in the direction of the arrows;

FIG. 8 of the drawings is a side elevational view of the inner cannula portion according to the present invention;

FIG. 9 of the drawings is a side elevational view, opposite the side elevational view of FIG. 8, of the inner cannula according to the present invention;

FIG. 10 of the drawings is a cross-sectional view of FIG. 8 taken along the lines 10—10 and looking in the direction of the arrows;

FIG. 11 of the drawings is a cross-sectional view of FIG. 8 taken along the lines 11—11 and looking in the direction of the arrows;

FIG. 12 of the drawings is a cross-sectional view of FIG. 2 taken along the lines 12—12 and looking in the direction of the arrows;

FIG. 13 of the drawings is a cross-sectional view of FIG. 3 taken along the lines 13—13 and looking in the direction of the arrows;

FIG. 14 of the drawings is a cross-sectional view of FIG. 13 taken along the lines 14—14 and looking in the direction of the arrows;

FIG. 15 of the drawings is a perspective view of the inner cannula tissue receiving region holding a tissue sample with the ejector rod in pre-depressed position according to the present invention; and FIG. 16 of the drawings is a side elevational view of the inner cannula with ejector rod in fully depressed position, ejecting the tissue sample from the inner cannula according to the present invention.

DETAILED DESCRIPTION OF THE INVENTION

While this invention is susceptible of embodiment in many different forms, there is shown in the drawings, and will herein be described in detail, one specific embodiment, with the understanding that the present disclosure can be considered as an exemplification of the principles of the invention and is not intended to limit the invention to the embodiment illustrated.

Bone marrow biopsy needle 20 is shown in FIG. 1 as comprising outer cannula 22, inner cannula 24, obturator 26, and ejector rod 28. As can also be seen in FIGS. 4–7, outer cannula 22 consists of a substantially cylindrical tube having both proximal end 30 and distal end 32. Outer cannula 22 has a hollow cross section between the proximal and distal ends, with a pre-determined inner diameter to accept inner cannula 24 (discussed in detail below). Although having a substantially uniform outer diameter, the outer cannula is internally tapered at distal end 32 such that distal end inner diameter 38 is smaller than proximal end inner diameter 36. The inward taper at distal end 32 further defines tissue engaging region 40.

Distal end 32 of outer cannula 22 is formed into a saddle point configuration 42 with sharp edges. Such a configuration facilitates cutting through both soft and hard tissue, thus allowing the bone biopsy needle to enter a bone marrow sampling region.

Conversely, proximal end 30 of outer cannula 22, depicted in FIG. 1, is affixed to T-shaped handle 44. The T-shaped handle further consists of bore hole 46 and a locking means. Bore hole 46 preferably has an inside diameter substantially equivalent to the outer cannular proximal end inside diameter 36, to allow free slidability of inner cannula 24 therethrough.

The locking means preferably comprises a ridge or tube 48 configured to cooperate with a flexible detent, such as grippers 60, associated with the handle of obturator 26 or inner cannula 24 (described below). Such a combination of ridge and flexible detent creates a tactile locking device which allows a user to feel the locking position when inner cannula 24 or obturator 28 is fully inserted into outer cannula 22. This locking, in turn, provides a physician with greater needle control, and protects the various biopsy needle component combinations against untimely disengagement. The locking means may also comprise T-shaped handle 44 being configured so as to lock together with a corresponding obturator or inner cannula handle. Moreover, the locking means may further consist of an additional hole or slot 49, configured to house an outwardly protruding detent, for instance detent 58, associated with the handle of either attached obturator 26 or inner cannula 28. Of course, while FIG. 1 shows the prefer red T-shaped handle, any conventional handle which allows easy gripping and manipulation of the outer cannula is likewise contemplated.

Inner cannula 24, shown in FIGS. 1 and 8–11, also consists of a cylindrical tube having both proximal end 50 and distal end 52. Inner cannula 24 has a hollow cross section between the proximal and distal ends, with a pre-determined outer diameter 55 that is narrower than inner diameter 36 of outer cannula proximal end 30, yet wider than inner diameter 32 of outer cannula distal end 32. Accordingly, outer diameter 55 allows inner cannula 24 to remain freely slidable within outer cannula proximal end 30, but also forces inner cannula 24 to encounter interference upon reaching tapered tissue engaging region 40 of outer cannula distal end 32.

Proximal end 50 of inner cannula 24 is affixed to T-shaped handle 56 (FIG. 1), so as to lock together with outer cannula T-shaped handle 44 upon complete advancing therein. Such a locking orientation—consisting not only of the configuration of the handle, but also a detent 58 configured to fit within hole 49 of T-shaped handle 44 and flexible grippers 60 designed to lock ridge 48 also of T-shaped handle 44—assures that the two cannulas move together, while also preventing inadvertent separation thereof.

Moreover, T-shaped handle 56 further consists of bore hole 62, preferably having an inner diameter substantially equivalent to the inner diameter of inner cannula 24. Bore hole 62 allows insertion of ejector rod 28 into inner cannula 24, as will be discussed below.

Referring once again to FIGS. 8–11, distal end 52 of inner cannula 24 further consists of tissue receiving region 64 having at least two or more interruptions, such as slits 68 and 70, in the continuity of the inner cannula. At least two of the interruptions are different from one another in at least one of configuration and orientation to alter the malleable memory of the tissue receiving portion of the inner cannula. These interruptions further define a tissue grasping member 65.

Tissue grasping member 65 comprises resilient deformable wall 66, first slit 68, second slit 70, distal edge 71 and spanning member 72. First slit 68 is positioned in a first side of resilient deformable wall 66 and extends from the distal edge 71 toward proximal end 50 of the inner cannula. Second slit 70 is positioned in a second side of resilient deformable wall 66, preferably displaced approximately 180 degrees from first slit 68. Preferably, first slit 68 and second slit 70 are aligned in substantial registration and are substantially equivalent in length, although differing lengths are certainly contemplated. However, unlike first slit 68, second slit 70 extends toward proximal end 50 of the inner cannula from a point slightly displaced from distal edge 71, thus defining spanning member 72. Spanning member 72 connects both sides of second slit 70, thus providing the tissue grasping member with increased structural integrity. Indeed, while the first and second slits provide the tissue grasping member with flexibility and deformability, the spanning member imparts the structural strength and malleability needed for the tissue grasping member to not only retain a biopsy tissue sample, but also to allow the tissue grasping member to return to its pre-biopsy shape after deformation. To this end, spanning member 72 is malleable to both tissue grasping and tissue releasing orientations.

Obturator 26, shown in FIG. 1, comprises a substantially cylindrical rod having proximal end 80 and distal end 82. Obturator 26 is of a solid construction, with an outer diameter pre-determined to be freely and operably slidable within outer cannula 22. Distal end 82 consists of cutting point 86, which works in combination with saddle point 42 of outer cannula 22 to assist a user in inserting the outer cannula into a desired biopsy region. Proximal end 80 is affixed to a substantially T-shaped handle 88, is of the same interlocking configuration as inner cannula T-shaped handle 56 described above. Preferably, as is illustrated in FIG. 2, distal end 82 of obturator 26 extends beyond and seals distal end 32 outer cannula 22, thus preventing any tissue from prematurely entering the outer cannula upon insertion into a patient.

Ejector rod 28, depicted in FIG. 1, comprises a substantially cylindrical rod having proximal end 90 and distal end 92. Like obturator 26, ejector rod 28 is of a solid construction, with an outer diameter pre-determined to be freely and operatively slidable within inner cannula 24.

Proximal end 90 is preferably affixed to ejector knob 96, which is associated with spring 98. While spring 98 is preferably of such a size so that the ejector rod does not interfere with the biopsy procedure (see FIGS. 13–15), the ejector rod is of a sufficient length so that distal end 92 extends past distal end 52 of inner cannula 24 upon compression of ejector knob 96 (see FIG. 16). Proximal end 90 may take any shape as would be capable of ejecting tissue sample from inner cannula 24.

In operation, and as is shown in FIGS. 2–3 and 12–14, obturator 26 is inserted and locked into outer cannula 22. This combination, preferably in a locked orientation, is then inserted into a biopsy tissue sampling region 100 of a patient in a conventional manner. Once outer cannula 22 reaches tissue sampling region 100, obturator 26 is withdrawn. Upon withdrawal, outer cannula 22 is advanced forward into bone marrow 102, causing a sample of the marrow tissue 104 to enter distal end 32.

At this point, inner cannula 24 is inserted into proximal end 30 of outer cannula 22 and slid toward distal end 32 thereof. Likewise, ejector rod 28 is preferably disposed within inner cannula 24 to facilitate eventual ejection of biopsy sample 104 from the inner cannula. Ejector rod 28 is spring-biased toward the proximal end of the inner cannula such that it does not interfere with the biopsy procedure.

Upon reaching the tapered engaging region 40 of outer cannula 22, inner cannula tissue grasping member 65 approaches distal edge 71 of outer cannula 22 and tissue receiving portion 64 approaches tissue sample 104. Substantially simultaneously, resilient deformable wall 66 of tissue grasping member 65 deforms inwardly under force of the inner walls of the tapered engaging region of outer cannula 22 to a tissue grasping orientation, while tissue receiving portion 64 receives tissue therewithin.

Upon complete advance of inner cannula 24 into outer cannula 22, tissue grasping member 65 is pinched at least partially closed, thus isolating and severing tissue sample 104 from tissue sampling region 102. At this point, tissue sample 104 is retained in tissue grasping member 65 of inner cannula 24. Additionally, upon complete advance of inner cannula 24 into the outer cannula 22, the outer and inner cannulas are locked together, preventing any relative rotation therebetween. Indeed, neither additional rotation of the inner cannula relative to the outer cannula, or vice versa, nor additional vertical and/or horizontal movement of the cannula needles are required to sever the tissue sample from the tissue sampling region.

Next, inner cannula 24, either alone or in combination with outer cannula 22, is withdrawn from the patient. Upon removal of the inner cannula from the outer cannula, tissue sample 104, still housed in receiving portion 64 of the inner cannula, is ejected by depressing the ejector knob on ejector rod 28. By pressing down on the ejector knob, the spring-biasing is overcome and ejector rod 28 ejects tissue sample 104 onto a slide or other receiving article.

While ejecting tissue sample 104 from inner cannula 24, ejector rod 28 performs the additional function of reforming resilient deformable wall 66 of tissue grasping member 65 of the inner cannula to a tissue releasing orientation and its original pre-biopsy configuration. Indeed, tissue grasping member 65 is operatively deformed by the taper of the outer cannula engaging region during severing and isolating of the tissue sample. In particular, resilient deformable wall 66 and spanning member 72 are cinched to an at least partially closed orientation to help retain bone marrow tissue sample 104 in place until ejection. Ejector 28 rod serves to re-expand those cinched portions of the inner cannula back to their original pre-biopsy formation, so that another biopsy procedure may be performed. Indeed, because spanning member 72 acts as a bridge between the two sides of second slit 70, it allows the second slit to impart needed flexibility and deformability on tissue grasping member 65, while providing the structural integrity necessary for easily and readily returning the tissue grasping member to its original pre-biopsy configuration.

The foregoing description and drawings are merely to explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A bone marrow biopsy device for insertion into and through a mass of bone to retrieve a biopsy sample of bone marrow tissue, said bone marrow biopsy device comprising:

an outer cannula, said outer cannula having a proximal end, a distal cutting end and a substantially hollow cross-section between said proximal and distal ends, said substantially hollow cross-section having a predetermined inner diameter that tapers inwardly proximate said distal end to form a tissue engaging region within said distal end;

an inner cannula operably slidable within said hollow cross-section of said outer cannula, said inner cannula having a proximal end, a distal end and a substantially hollow tissue receiving portion proximate said inner cannula distal end for retrieving at least a portion of a tissue sample from within the tissue engaging region of said outer cannula, said inner cannula having a predetermined outer diameter slightly narrower than said predetermined inner diameter of said outer cannula except at said tissue engaging region where said tapered distal end of said outer cannula is of a diameter less than that of said inner cannula prior to deformation of said inner cannula distal end by said outer cannula distal end, said tissue receiving portion of the inner cannula distal end further having both a continuity of structure and a malleable memory; and at least two or more interruptions in the continuity of the structure of the tissue receiving portion of the inner cannula, at least two of said two or more interruptions being different from each other in at least one of configuration and orientation to alter the malleable memory of said tissue receiving portion of the distal end of said inner cannula and to define a tissue grasping member that constricts upon said deformation of said inner cannula distal end, said tissue grasping member of said inner cannula constricting within the distal end of said outer cannula to, in turn, grasp a tissue sample positioned therewithin, upon operable engagement between the inwardly tapered tissue engaging region of said outer cannula and the tissue grasping member of said inner cannula.

2. The invention according to claim 1 wherein said at least two or more interruptions in the tissue receiving portion of said inner cannula distal end define a tissue grasping member, said tissue grasping member comprises:

at least one resilient deformable wall for grasping a biopsy tissue sample upon said deformation upon compression of said distal end of said tissue receiving portion caused by operable engagement between an inner face of said engaging region and an outer surface of said grasping member;

means for selectively maintaining and alternatively releasing said compressed configuration of said at least one resilient deformable wall so as to positively retain and release said biopsy tissue sample within said tissue grasping member through deformation between a tissue grasping and a tissue releasing orientation, said means for selectively maintaining and alternatively releasing said compressed configuration of said at least one resilient deformable wall comprising at least two slits positioned in said resilient deformable wall and a spanning member traversing at least one of the slits.

3. The invention according to claim 2 wherein said tissue grasping member further comprises:

a first slit in a first side of said resilient deformable wall of said inner cannula, said first slit extending from the furthest limit of said distal end toward said proximal end;

a second slit in a second side of said resilient deformable wall of said inner cannula, said second slit being displaced substantially 180 degrees from said first slit such that said first and second slits are aligned in substantial opposed registration to each other, said second slit extending from a position between said distal and proximal ends of said inner cannula to a position displaced slightly axially from said distal end where said second slit is interrupted by said spanning member, said spanning member located substantially proximate said distal end of the said inner cannula at said end of said second slit, said spanning member substantially connecting both sides of said second slit, said spanning member further being substantially malleable to both said tissue grasping and said tissue releasing orientations.

4. The invention according to claim 3 wherein said first and second slits have substantially the same length and are skewed axially with respect to one another.

5. The invention according to claim 3 wherein said spanning member is integral to said resilient deformable wall.

6. The invention according to claim 3 wherein said inner cannula is completely slidably removable from said outer cannula.

7. The invention according to claim 6 wherein said bone marrow biopsy device further includes a removable obturator, said removable obturator being freely and operably slidable within said outer cannula and substantially sealing said distal end.

8. The invention according to claim 3 wherein said inner cannula is a substantially right cylindrical, hollow tube having a predetermined outer diameter larger than said predetermined inner diameter of said engaging region of said outer cannula.

9. The invention according to claim 3 further including an ejector rod operably disposed within said inner cannula to facilitate ejection of said biopsy tissue sample from said distal end of said inner cannula and to expand said resilient deformable wall.

10. The invention according to claim 9 wherein said ejector rod is spring-biased toward said proximal end of said inner cannula such that said ejector rod does not interfere with said compression of said resilient deformable wall.

11. The invention according to claim 1 further comprising an outer T-shaped handle affixed to said outer cannula proximal end.

12. The invention according to claim 11 further comprising an inner T-shaped handle affixed to said inner cannula proximal end, wherein said outer and inner T-shaped handles are configured so as to lock together to prevent relative rotation between said inner and outer cannulas.

13. The invention according to claim 11 further comprising an inner handle affixed to said inner cannula proximal end, wherein said inner handle and outer T-shaped handle are configured so as to lock together to prevent relative rotation between said inner and outer cannulas.

14. The invention according to claim 1 further comprising an outer handle affixed to said outer cannula proximal end.

15. The invention according to claim 14 further comprising an inner T-shaped handle affixed to said inner cannula proximal end, wherein said outer handle and said inner T-shaped handle are configured so as to lock together to prevent relative rotation between said inner and outer cannulas.

16. The invention according to claim 1 wherein said inner cannula is a substantially cylindrical hollow tube having a predetermined outer diameter larger than said predetermined inner diameter of said tissue engaging region of said outer cannula.

17. The invention according to claim 1 further including an ejector rod operably disposed within said inner cannula to facilitate ejection of said biopsy tissue sample from said distal end of said inner cannula and to expand said resilient deformable wall.

18. The invention according to claim 17 wherein said ejector rod is spring-biased toward said proximal end of said inner cannula such that said ejector rod does not interfere with said compression of said resilient deformable wall.

19. The invention according to claim 1 wherein said outer cannula distal end further consists of a saddle point configuration.

* * * * *

UNITED STATES PATENT AND TRADEMARK OFFICE
CERTIFICATE OF CORRECTION

PATENT NO. : 6,063,037
DATED : May 16, 2000
INVENTOR(S) : Mittermeier et al.

It is certified that error appears in the above-identified patent and that said Letters Patent is hereby corrected as shown below:

<u>Column 5,</u>
Line 4, change "prefer and red" to -- preferred --

Signed and Sealed this

Sixteenth Day of April, 2002

Attest:

Attesting Officer

JAMES E. ROGAN
*Director of the United States Patent and Trademark Office*